US011852283B2

(12) United States Patent
Sauer

(10) Patent No.: US 11,852,283 B2
(45) Date of Patent: Dec. 26, 2023

(54) TORQUE ENHANCING APPARATUS

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 71 days.

(21) Appl. No.: 17/617,362

(22) PCT Filed: Jun. 12, 2020

(86) PCT No.: PCT/US2020/037430
§ 371 (c)(1),
(2) Date: Dec. 8, 2021

(87) PCT Pub. No.: WO2020/252258
PCT Pub. Date: Dec. 17, 2020

(65) Prior Publication Data
US 2022/0252212 A1    Aug. 11, 2022

Related U.S. Application Data

(60) Provisional application No. 62/860,563, filed on Jun. 12, 2019.

(51) Int. Cl.
*F16M 11/20*    (2006.01)
*F16M 13/02*    (2006.01)
*A61B 90/50*    (2016.01)

(52) U.S. Cl.
CPC ...... *F16M 11/2078* (2013.01); *F16M 13/022* (2013.01); *A61B 90/50* (2016.02)

(58) Field of Classification Search
CPC .. A61B 90/50; F16M 11/2078; F16M 13/022; B25B 17/02; B25B 23/0028
USPC ........................................... 248/274.1
See application file for complete search history.

(56) References Cited

U.S. PATENT DOCUMENTS

| 6,055,889 | A  | * | 5/2000  | Rinner ............... B25G 3/06 81/177.85 |
| 2003/0079575 | A1 | * | 5/2003  | Blanco Guajardo ... B25B 17/02 81/177.75 |
| 2009/0255386 | A1 | * | 10/2009 | Liao ................... B25B 23/1427 81/124.5 |
| 2013/0199343 | A1 | * | 8/2013  | Crewe ................. B25F 1/02 81/439 |
| 2016/0207181 | A1 | * | 7/2016  | Coffland ............ B25B 23/0028 |

* cited by examiner

*Primary Examiner* — Todd M Epps
(74) *Attorney, Agent, or Firm* — Michael E. Coyne

(57) ABSTRACT

The torque enhancing apparatus including a first socket and a second socket coupled to the first socket, including an extendable moment arm. The torque enhancing apparatus includes a ball pivotably and captively held between the first socket and the second socket. The torque enhancing apparatus may include one or more extendable moment arms. The extendable moment arm or arms are configured such that they provide a mechanical advantage for moving the first socket and the second socket relative to one another. The torque enhancing apparatus may include a first socket, a second socket coupled to the first socket including four extendable moment arms. The torque enhancing apparatus including a ball pivotably held between the first socket and the second socket.

13 Claims, 7 Drawing Sheets

TORQUE ENHANCING APPARATUS

REFERENCE TO RELATED APPLICATIONS

This application is a national stage application, filed under 35 U.S.C. § 371, of International Patent Application No. PCT/US20/37430, filed on Jun. 12, 2020, which claims priority to U.S. Provisional Patent Application No. 62/860,563, filed Jun. 12, 2019, the contents of each of which is hereby incorporated by reference in its entirety.

FIELD

The claimed invention relates to mounting apparatuses, and more specifically to mounting apparatuses for instrumentation.

BACKGROUND

In a variety of leisure activities and professional procedures it can be cumbersome for an individual to simultaneously handle and configure instrumentation, particularly when more than one device is in use. In a surgical example, laparoscopic, endoscopic, and other types of minimally invasive surgical procedures often rely on percutaneous introduction of surgical instruments into an internal region of a patient where the surgical procedure is to be performed. Surgeons continue to find it desirable to utilize smaller and smaller access incisions in order to minimize trauma and reduce patient recovery times. Frequently, surgeons will make additional small incisions through which a viewing scope or other surgical equipment may be passed to assist in the operation. In the case of viewing scopes, an assistant may manipulate and/or hold the scope in a fixed position for the surgeon so that the surgeon may look at images, acquired by the scope, on a monitor screen in order to perform the minimally invasive operation. Equipment holders may be used in lieu of an assistant to position and hold surgical equipment such as, but not limited to, a viewing scope.

Other industries are also beset with the similar dilemma of having the capability to reliably and adjustably mount one or more instruments or instrumentation holders. While instrumentation holders are known to those skilled in the art, easily adjustable mounts with enhanced mechanical function are not as prevalent. Therefore, it would be desirable to have a mounting apparatus providing enhanced torque for adjustably mounting various instrumentation.

SUMMARY

A torque enhancing apparatus is disclosed. The torque enhancing apparatus includes a first socket and a second socket coupled to the first socket, including an extendable moment arm. The torque enhancing apparatus also includes a ball pivotably held between the first socket and the second socket.

The torque enhancing apparatus may also include two or four extendable moment arms. The extendable moment arms are configured such that they provide a mechanical advantage for moving the first socket and the second socket relative to one another.

Another torque enhancing apparatus is disclosed. The torque enhancing apparatus includes a first socket, a second socket coupled to the first socket including four extendable moment arms. The torque enhancing apparatus also includes a ball pivotably held between the first socket and the second socket.

Figure 1A:
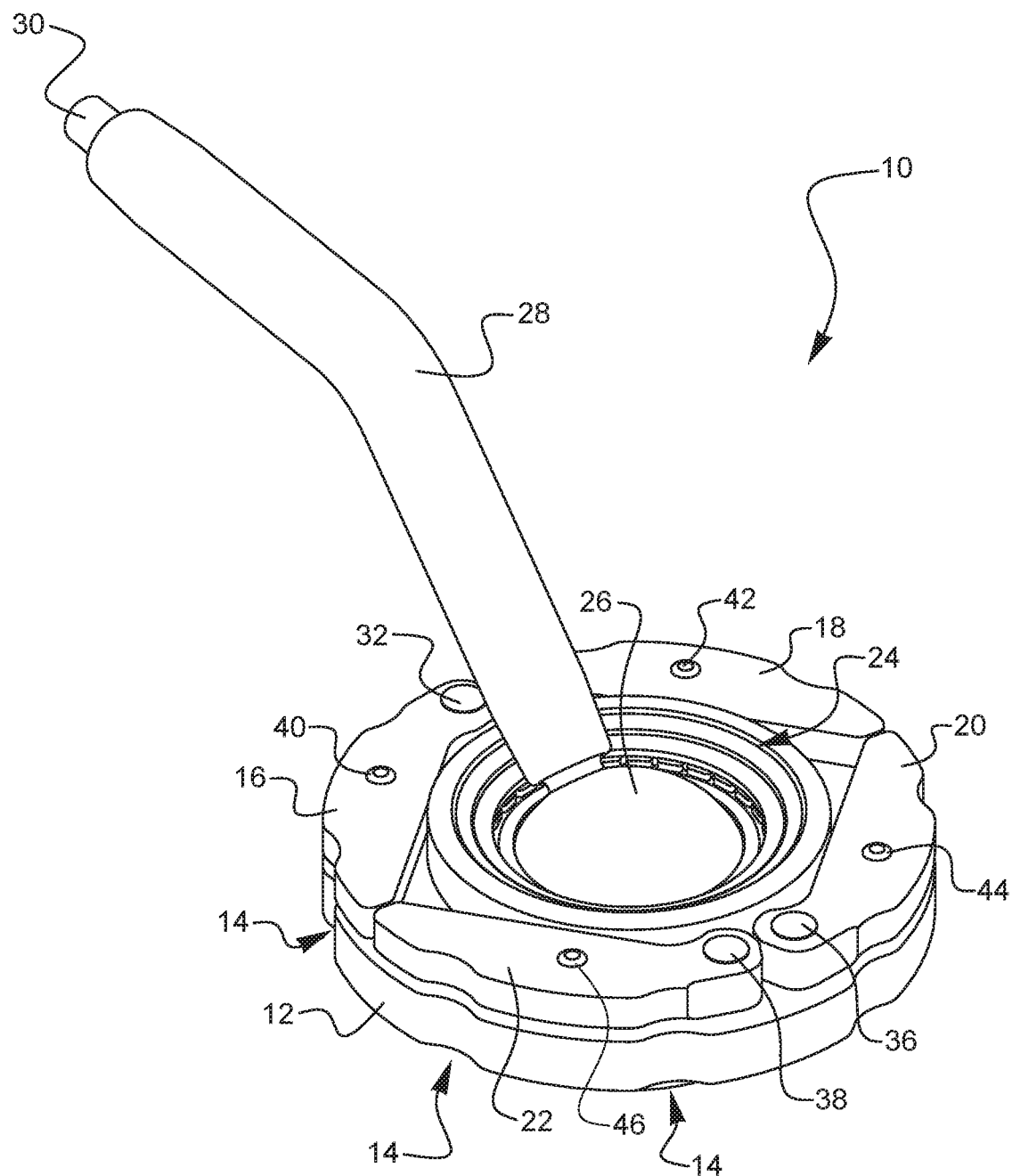
FIG. 1A is a top-front perspective view of a torque enhancing apparatus.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2A:
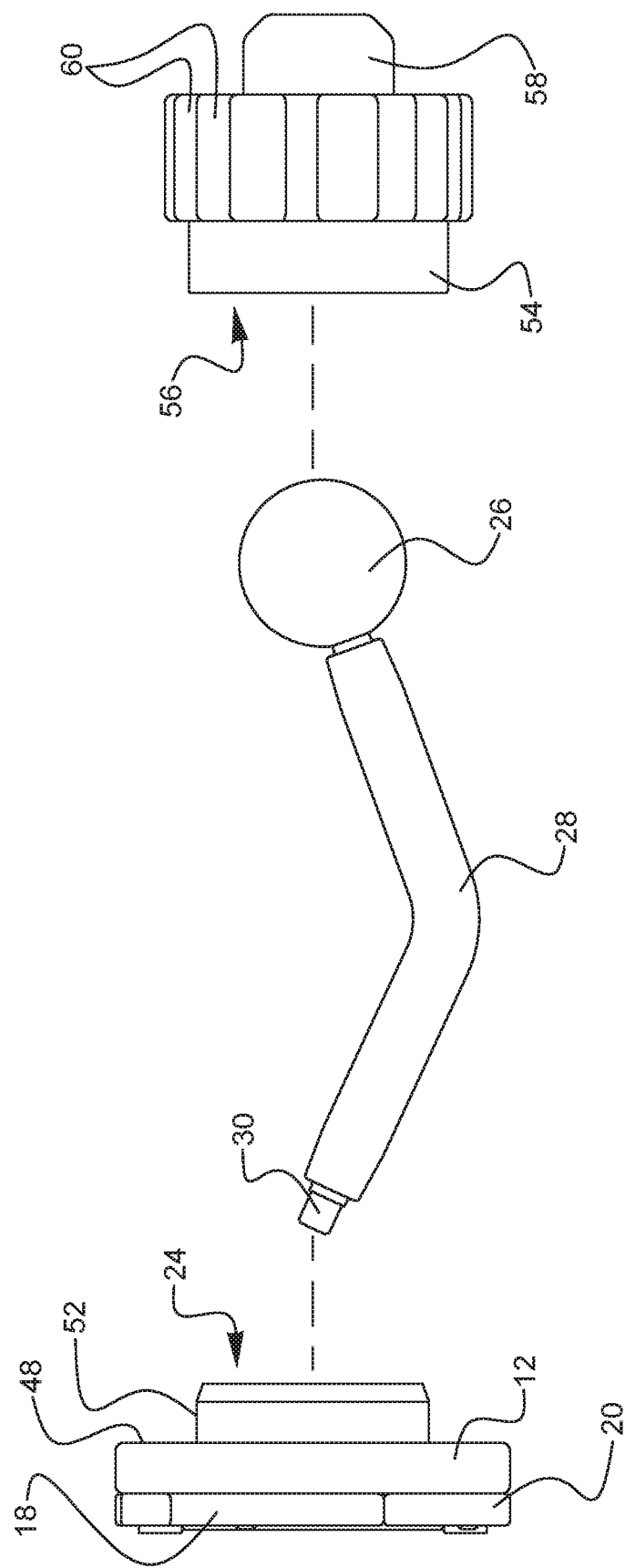
FIG. 2A is an exploded view of the assembly of the torque enhancing apparatus of FIG. 1A.

FIG. 1A is a top-front perspective view of a torque enhancing apparatus. This view of the torque enhancing apparatus 10 illustrates a disc-shaped second socket 12. The disc-shaped second socket interfaces via screw thread with a first socket 54, which is not shown in this view but which is illustrated in FIG. 2A. Further details of the first socket and the interface between the first socket 54 and the second socket 12 will be discussed later. The edges of the disc-shaped second socket 12 have several recesses 14 in a rounded scallop shape which act as an ergonomic feature and are configured for an improved ergonomic grip. Other embodiments of a similar apparatus may have recesses of alternate shapes, orientations or sizes. Four extendable moment arms 16, 18, 20, 22, shown in a retracted position, are pivotably coupled to the second socket 12, each by way of their respective pivots 32, 34, 36, 38 and are retractable to a position substantially within the outer circumference of the second socket 12. Each extendable moment arm 16, 18, 20, 22 defines a retainer 40, 42, 44, 46 therein. Each retainer may also be referred to as a retaining feature, or biasing restraint, as the retainer is configured to bias against a corresponding feature in the flange 48 (not visible here, but shown later) of the second socket 12 and thereby hold each extendable moment arm 16, 18, 20, 22 in place in its retracted position until the biased retaining force is defeated and the arms 16, 18, 20, 22 are purposefully extended. Held within a central socket recess 24 defined by the second socket 12 is a ball 26 coupled to a mounting arm 28. The mounting arm 28 is bent at a 135 degree angle and a stub or connector 30 is located on the mounting arm 28 on the end opposite that of the ball 26. The connector 30 is a potential attachment point for another ball, fixed instrument, or other device in alternate embodiments or configurations. Either end of the mounting arm 28 could have screw threads, welded joints, or other means of attachment known to those skilled in the art. Alternate embodiments of the mounting arm 28 may be straight, may have bends of other angles advantageous for a particular application of instrument or device, or may be of varying lengths suitable to a particular use or application. The ball 26 is captively held between the second socket 12 and a first socket 54 (illustrated in FIG. 2A). The ball 26, and therefore the mounting arm 28 and any instrument or attachment fixed thereto, is movable when the first socket 54 and second socket 12 are loosened relative to one another. The ball 26, and therefore the mounting arm 28 and any instrument or attachment fixed thereto, is held in a fixed location when the mounting arm 28 is placed in a desired position and the first socket 54 and second socket 12 are tightened relative to one another. As shown in its retracted position in FIG. 1A, the torque enhancing apparatus may be difficult to tighten for all users, or may require a higher measure of tightening force if heavier instrumentation is affixed to the mounting arm 28. Further, it may be of critical importance to a procedure or operation that instrumentation affixed to the mounting arm 28 and tightened by the torque enhancing apparatus 10 remain as immobile as possible for the duration of said procedure or operation. Other embodiments of a torque enhancing apparatus may have only one extendable moment arm, or more than four extendable moment arms with varying shapes or orientations. The two opposite pairs include a first pair of extendable moment arms 16, 20 and a second pair of extendable moment arms 18, 22. As shown, both pairs of extendable moment arms are substantially symmetrical, or form a symmetrical shape whether extended or retracted. Alternate embodiments may incorporate asymmetric arrangements of extendable moment arms.

Figure 1B:
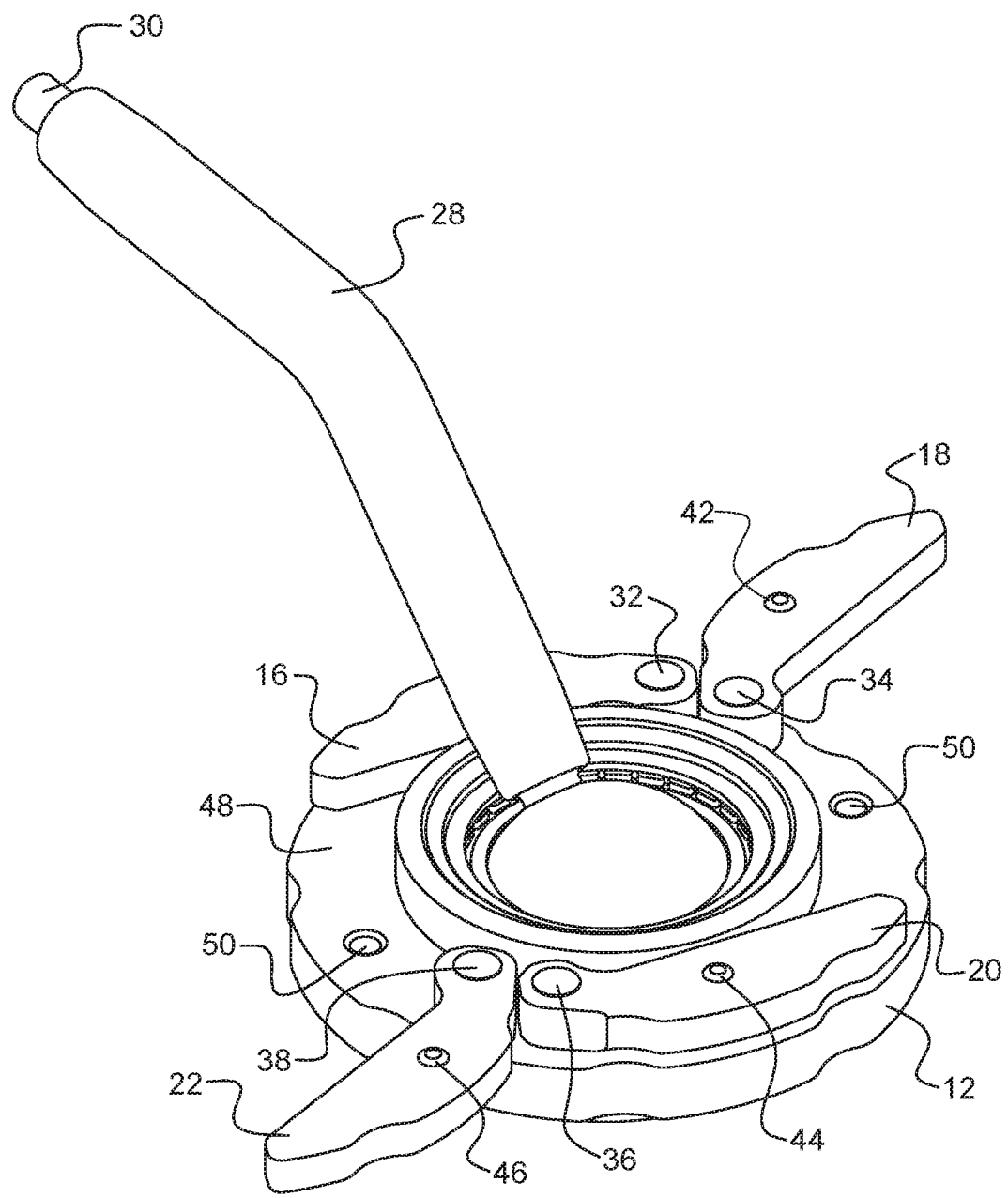
FIG. 1B is a top-front perspective view of the torque enhancing apparatus of FIG. 1A with two moment arms extended.

FIG. 1B is a top-front perspective view of the torque enhancing apparatus of FIG. 1A with two moment arms extended. There are two extendable moment arms 18, 22 shown in an extended position, pivoting outward from their retracted position within the second socket 12 that was illustrated in FIG. 1A. Also shown are two of the four recesses 50 located in a flange 48 on the second socket 12 of the torque enhancing apparatus 10. These recesses 50 correspond to and are configured to engage with each of the retainers 40, 42, 44, 46 on their respective extendable moment arms 16, 18, 20, 22 to hold each of the extendable moment arms 16, 18, 20, 22 in place until such time as they are needed to assist a user in tightening or loosening the torque enhancing apparatus. By applying a minimal amount of force to rotate the pair of extendable moment arms 18, 22, the retainers 46, 42 can be defeated and the arms 18, 22 rotated into their extended position. In this extended configuration, the two extendable moment arms 18, 22 provide a larger radius for a contact point of applied force by an operator as compared to the radius of the second socket with the moment arms 18, 22 retracted relative to a central point in the disc-shaped second socket 12, and thus a reduced amount of input force is necessary to rotate the second socket 12 in a clockwise direction and achieve a similar output force when the extendable moment arms 18, 22 are extended. This increased radius of contact point, and thus reduced force, allows a user to apply an increased amount of torque for the purpose of tightening or loosening the torque enhancing apparatus 10.

Figure 2B:
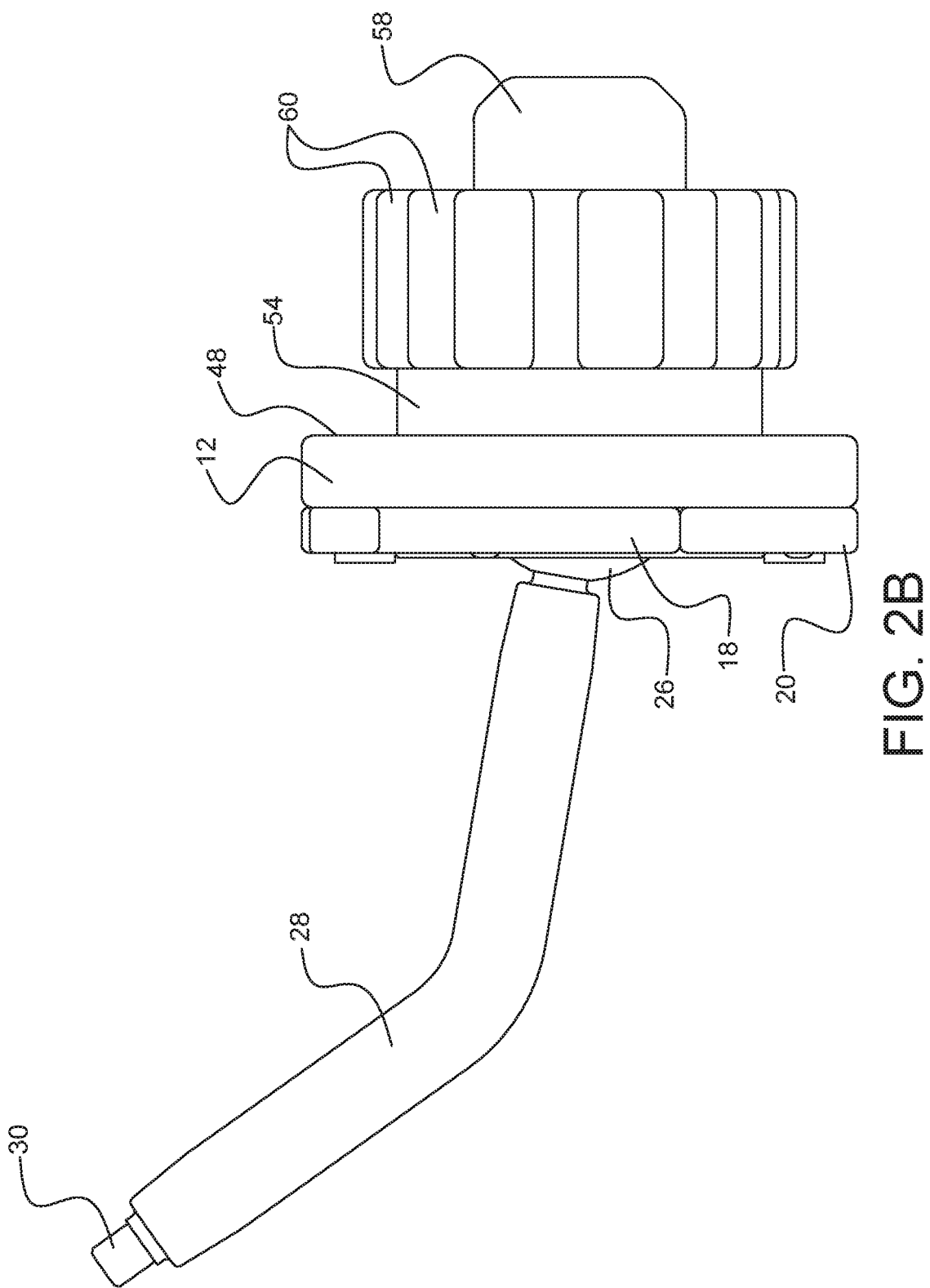
FIG. 2B is an assembled side view of the torque enhancing apparatus of FIG. 1A.

FIG. 2A is an exploded view of the assembly of the torque enhancing apparatus of FIG. 1A. The second socket 12 defines a lower portion of the second socket 52, a flange 48, and four extendable moment arms 18, 20 pivotably coupled to the flange 48. The disc-shaped second socket 12 defines a central socket recess 24 that extends therethrough. The central socket recess 24 defines inner threads that are not visible in this view. The connection end or connector 30 of the mounting arm 28 is inserted into and through the central socket recess 24 on the second socket 24. The central socket recess 24 is configured to receive and pivotably constrain the ball 26 end of the mounting arm 28 once the arm 28 is passed through the central socket recess 24 of the second socket 12. The diameter of the ball 26 is larger than the diameter of the central socket recess 24, and thus cannot fully pass through the second socket 12. The central socket recess 24 also defines an inner wall having threads and an outer wall, which are not shown in this view. A first socket 54 defines a socket mount 58, configured for attachment of the torque enhancing apparatus 10 to a base, clamp, or other stationary object. Several knurls 60 are also defined by the first socket 54 for providing and ergonomic grip for tightening or attaching the first socket 54 to a base or clamp. Other embodiments may be attached to a base or a clamp by other means, such as fasteners, welding, adhesives, or other suitable methods known to those skilled in the arts. The first socket 54 also has a coupling recess 56 having threads (also not shown in this view) on the inner wall that mate with the threads within the central socket recess 24 of the second socket 12. The diameter of the ball 26 is also larger than the diameter of the shape of the central socket recess 24, and thus can be constrained between the second socket 12 and the first socket 54 when the second socket 12 and the first socket 54 are threaded together and tightened. The first socket 54 is placed over the ball 26 on the mounting arm 28 and threaded into the second socket 12. Upon some tightening of the interlocking threads of the first socket 54 and the second socket 12, the ball 26 is confined, movement of the ball 26 is prohibited, and pivotable motion of the mounting arm 28 and any further attachments is restricted. Upon further tightening, the ball 26 is further confined, and the mounting arm 28 can be rendered immobile. The coupling recess 56 on the first socket 54 is configured to hold the ball 26 on the mounting arm 28 captive. FIG. 2B is an assembled side view of the torque enhancing apparatus of FIG. 1A, showing the result of the assembly steps shown in FIG. 2A.

Figure 3A:
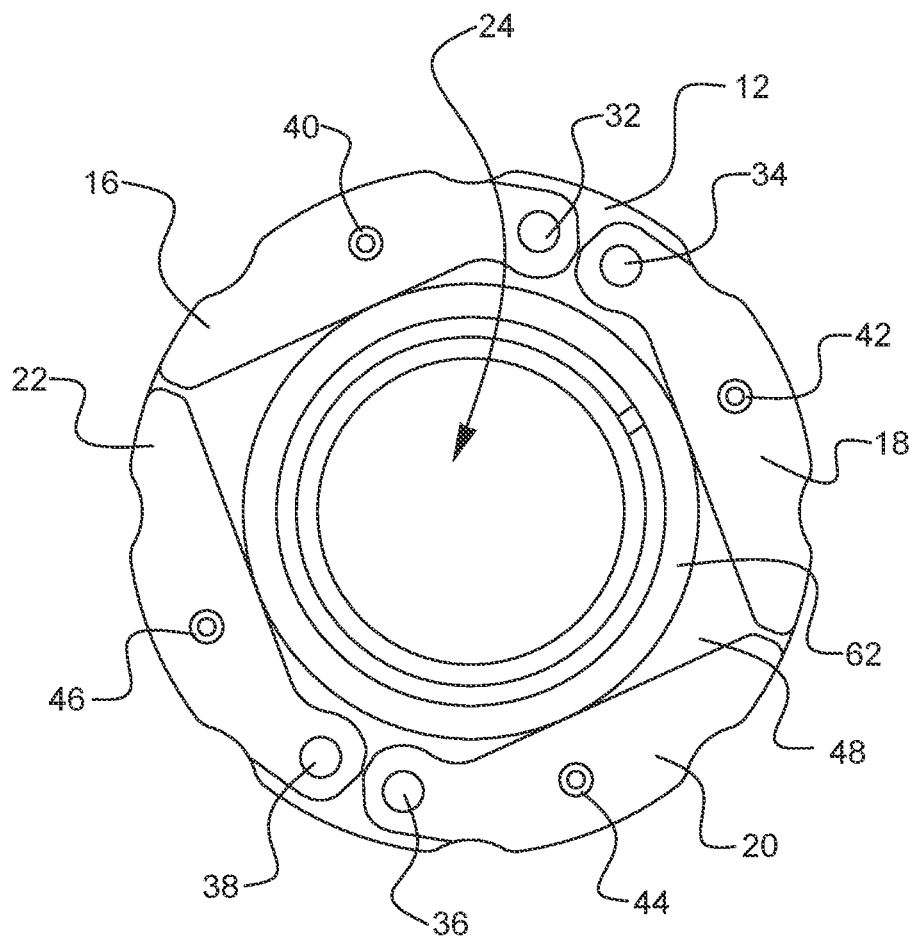
FIG. 3A-3C are top views of the torque enhancing apparatus of FIG. 1A with all four pair of moment arms retracted, one pair of moment arms extended, and another pair of moment arms extended, respectively.
Figure 3B:
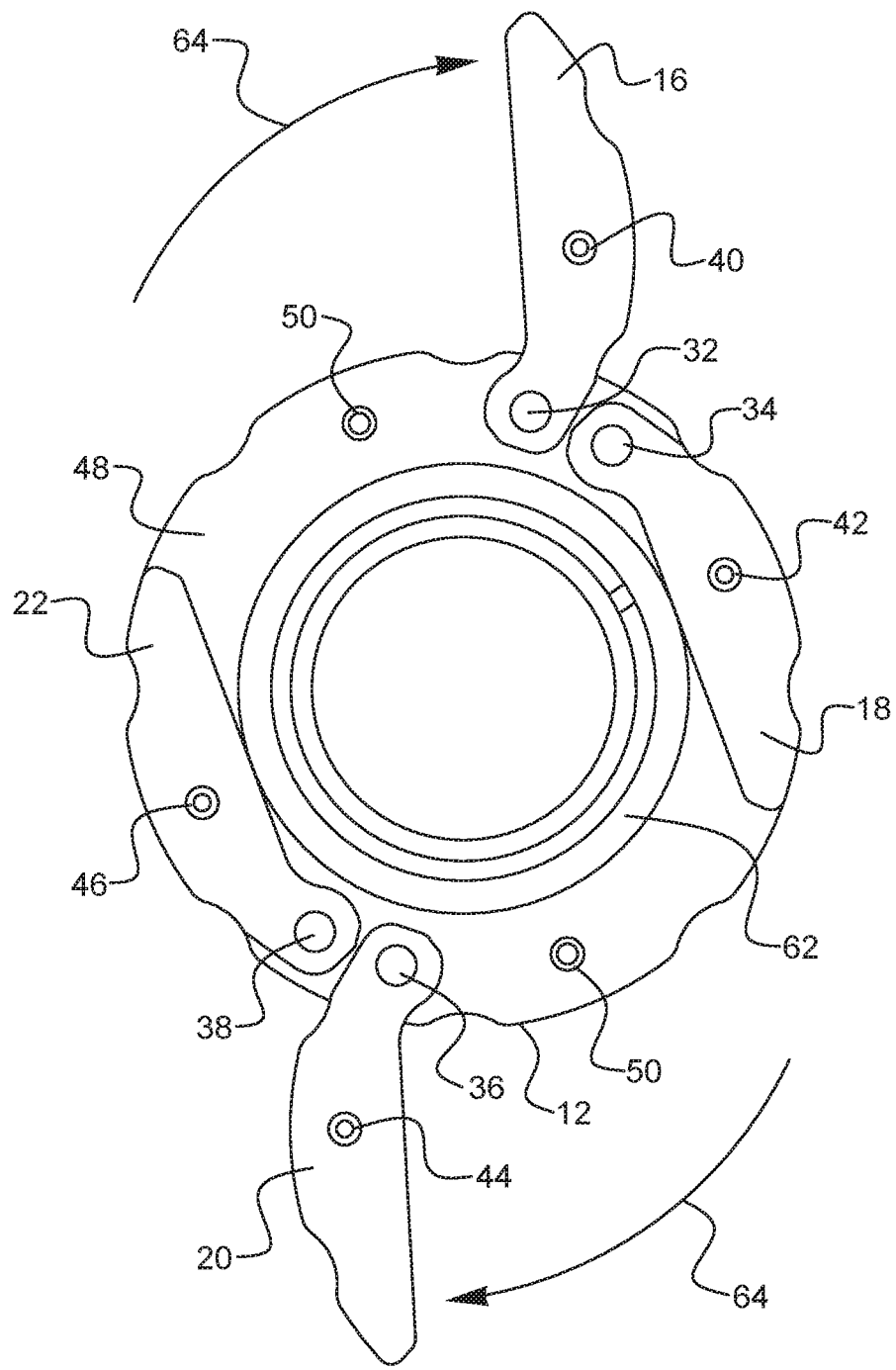
Figure 3C:
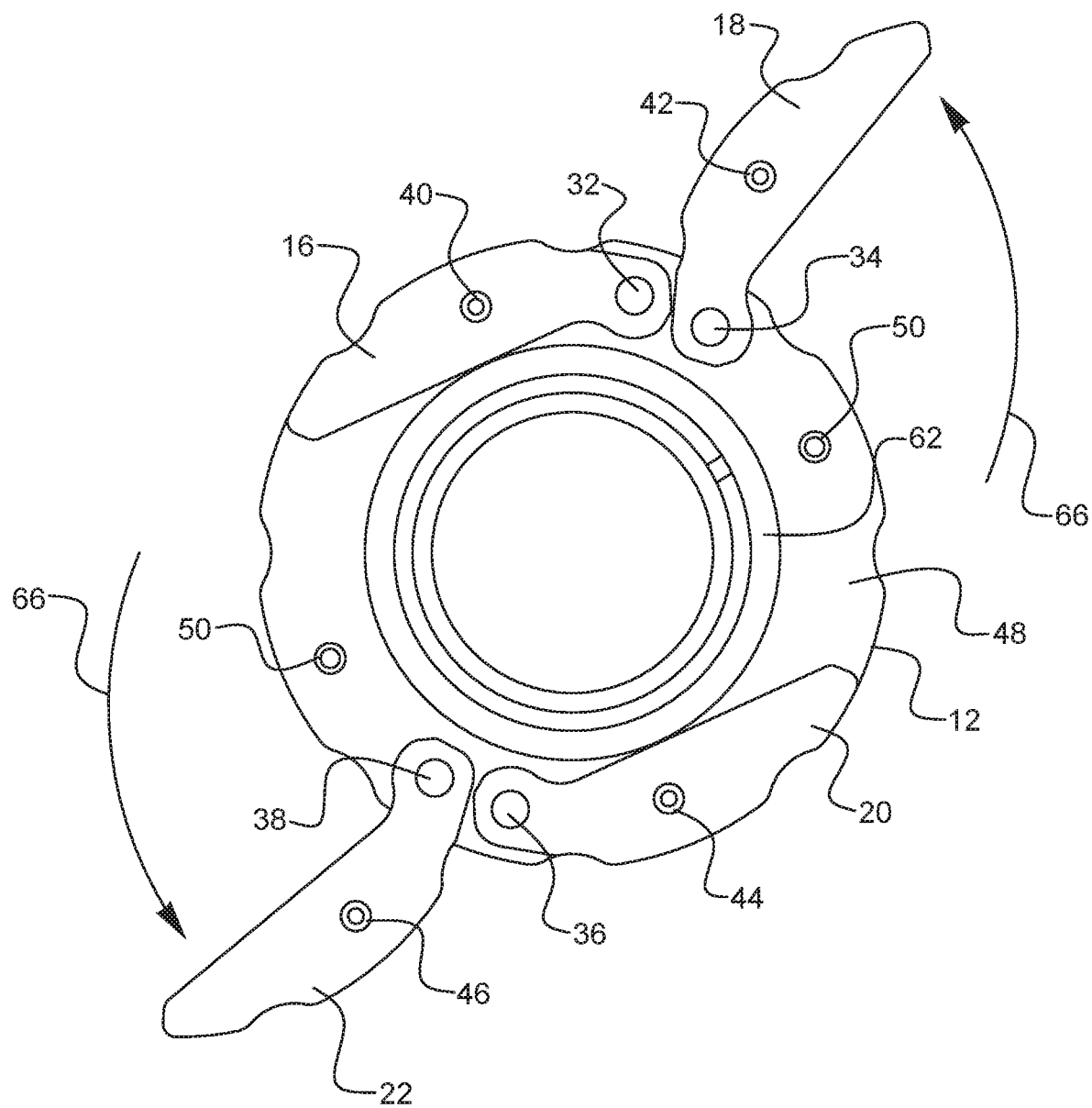

FIG. 3A-3C are top views of the torque enhancing apparatus of FIG. 1A with all four pair of moment arms retracted, one pair of moment arms extended, and another pair of moment arms extended, respectively. This embodiment of the torque enhancing apparatus 10 shown in FIG. 3A is shown from the top view, looking down onto the second socket 12. The ball and mounting arm are removed in FIGS. 3A-3C to show the features of the second socket more clearly. The torque enhancing apparatus 10 embodiment illustrates all four extendable moment arms 16, 18, 20, 22 in a retracted state. Two of the extendable moment arms are tightening extendable moment arms 16, 20 and two of the extendable moment arms are loosening extendable moment arms 18, 22. Each of the four extendable moment arms 16, 18, 20, 22 are held in the second socket with a pivot pin 32, 34, 36, 38 which permits each extendable moment arm to pivot outwardly. Each of the four extendable moment arms 16, 18, 20, 22 also have a biasing restraint or retainer 40, 42, 44, 46, in this embodiment, a spring loaded pin biased toward the flange 48 of the second socket 12, configured to restrain each extendable moment arm 16, 18, 20, 22 in the retracted position. A sufficient force must be applied to defeat each biasing restraint or retainer 40, 42, 44, 46 in order to extend each moment arm outward 16, 18, 20, 22. This embodiment shows a pair of loosening extendable moment arms 16, 20 and a pair of tightening extendable moment arms 18, 22 retracted within the outer circumference second socket 12, providing a mechanical advantage for tightening the first socket 54 and the second socket 12 relative to one another. Alternate embodiments may have other arrangements and orientations of extendable moment arms that may or may not overlap, may slide back and forth between retracted and extended positions, may be slidably attached to the second socket, may be detachable, or combinations thereof. FIG. 3B shows the torque enhancing apparatus of FIG. 3A with the two tightening extendable moment arms 16, 20 extended and the two loosening extendable moment arms 18, 22 retracted. The torque enhancing apparatus 10 may now be rotated in a clockwise direction 64 in order to tighten the ball 26 of the mounting arm 28 between the first socket 54 and the second socket 12 with reduced applied force as compared to when tightening the first socket 54 and second socket 12 with the extendable moment arms 16, 20 retracted. FIG. 3C shows the torque enhancing apparatus of FIG. 3A with the two loosening extendable moment arms 18, 22 extended and the two tightening extendable moment arms 16, 20 retracted, providing a mechanical advantage for loosening the first socket 54 and the second socket 12 relative to one another. The torque enhancing apparatus 10 may now be rotated in a counterclockwise direction 66 in order to loosen the ball 26 of the mounting arm 28 between the first socket 54 and the second socket 12 with reduced force as compared to when the loosening extendable moment arms 18, 22 are retracted. Alternate embodiments of the torque enhancing apparatus may be directionally oriented such that a clockwise rotation loosens the first and second socket relative to one another, and counterclockwise rotation tightens the first and second socket relative to one another.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:
1. A torque enhancing apparatus, comprising:
a mounting assembly comprising:
  a mounting arm extending from a first end to a second end; and
  a ball disposed at the second end of the mounting arm, the ball having a first diameter;
a first socket comprising:
  a first coupling portion having a first cylindrical surface, wherein at least a portion of the first cylindrical surface is threaded; and
  a first receiving enclosure having one or more circumferential walls that extend along a first socket axis and a support wall that extends substantially transverse to the first socket axis, the first receiving enclosure configured to receive at least a portion of the ball of the mounting assembly such that a first portion of the ball contacts a portion of the support wall;
a second socket comprising:
  a flange portion including a top surface that surrounds a first portion of a central aperture extending through the flange portion, the central aperture having a second diameter that is less than the first diameter;
  an elongated first moment arm that extends from a first end to a second end, the first end being pivotably coupled to a first portion of the flange portion, the first moment arm configured to be pivoted between a retraced position and an extended position, wherein when the first moment arm is in the extended position, the second end extends beyond an outer perimeter edge defining the flange portion, and wherein when the first moment arm is in the retracted position, the second end does not extend beyond the outer perimeter edge defining the flange portion;
  an elongated second moment arm that extends from a first end to a second end, the first end being pivotably coupled to a second portion of the flange portion, the second moment arm configured to be pivoted between a retraced position and an extended position, wherein when the second moment arm is in the extended position, the second end extends beyond the outer perimeter edge defining the flange portion, and wherein when the second moment arm is in the retracted position, the second end does not extend beyond the outer perimeter edge defining the flange portion; and
  a cylindrical second coupling portion projecting from the flange portion, the second coupling portion comprising:
    one or more inner surfaces that define a second portion of the central aperture;
    a second socket engagement portion disposed at an end portion of the second coupling portion; and
    a circumferential second cylindrical surface, wherein at least a portion of the second cylindrical surface is threaded, and wherein the threaded portion of the second cylindrical surface engages the threaded portion of the first cylindrical surface to displace the second socket between an engaged position and a disengaged position relative to the first socket, wherein:
    (a) when the second cylindrical surface is rotated in a first rotational direction relative to the first cylindrical surface, the second socket engagement portion of the second socket displaces in a first linear direction towards a second portion of the ball until the second socket engagement portion contacts the second portion of the ball such that the second socket is in the engaged position in which the ball is fixed between the second socket engagement portion and the support wall of the first receiving enclosure of the first socket, and
    (b) when the second cylindrical surface is rotated in a second rotational direction relative to the first cylindrical surface, the second socket engagement portion of the second displaces in a second linear direction away from the second portion of the ball until the second socket engagement portion is not in contact with the second portion of the ball such that the second socket is in the disengaged engaged position in which the ball is the rotatable relative to the first socket that thus the mounting arm is positionable relative to the first socket, and
  wherein each of the first moment arm and the second moment arm are configured to be rotated from the retraced position to the extended position such that a force is configured to be applied by a user to the second end of each of the first moment arm and the second moment arm to rotate the second socket from the disengaged position to the engaged position.

2. The torque enhancing apparatus of claim 1, further comprising a mount coupled to the first socket.

3. The torque enhancing apparatus of claim 1, wherein the second socket further comprises an ergonomic feature.

4. The torque enhancing apparatus of claim 3, wherein the ergonomic feature comprises a plurality of recesses.

5. The torque enhancing apparatus of claim 1, wherein the first moment arm and the second moment arm are symmetrically positioned relative to the central aperture.

6. The torque enhancing apparatus of claim 1, wherein the two extendable moment arms are asymmetrical.

7. The torque enhancing apparatus of claim 1, wherein the first moment arm and the second moment arm each rotate in a first pivot direction from the retracted position to the extended position.

8. The torque enhancing apparatus of claim 1, wherein a pivot axis of each of the first moment arm and the second pivot arm is parallel to the first socket axis.

9. The torque enhancing apparatus of claim 1, the second socket further comprising:
an elongated third moment arm that extends from a first end to a second end, the first end being pivotably coupled to a third portion of the flange portion, the third moment arm configured to be pivoted between a retraced position and an extended position, wherein when the third moment arm is in the extended position, the second end extends beyond the outer perimeter edge defining the flange portion, and wherein when the third moment arm is in the retracted position, the second end does not extend beyond the outer perimeter edge defining the flange portion; and
an elongated fourth moment arm that extends from a first end to a second end, the first end being pivotably coupled to a fourth portion of the flange portion, the fourth moment arm configured to be pivoted between a retraced position and an extended position, wherein when the fourth moment arm is in the extended position, the second end extends beyond the outer perimeter edge defining the flange portion, and wherein when the fourth moment arm is in the retracted position, the second end does not extend beyond the outer perimeter edge defining the flange portion,
wherein each of the third moment arm and the fourth moment arm are configured to be rotated from the retraced position to the extended position such that a second force is configured to be applied by the user to the second end of each of the third moment arm and the fourth moment arm to rotate the second socket from the engaged position to the disengaged position.

10. The torque enhancing apparatus of claim 9, wherein the first moment arm and the second moment arm each rotate in a first pivot direction from the retracted position to the extended position, and wherein the third moment arm and the fourth moment arm each rotate in a second pivot direction from the retracted position to the extended position, wherein the second pivot direction is opposite to the first pivot direction.

11. The torque enhancing apparatus of claim 9, wherein a pivot axis of each of the first moment arm, the second pivot arm, the third pivot arm, and the fourth pivot arm is parallel to the first socket axis.

12. The torque enhancing apparatus of claim 1, wherein the top surface of the flange portion is planar and normal to the first socket axis.

13. The torque enhancing apparatus of claim 1, wherein the first end of the mounting arm is configured to be coupled to a medical instrument.

* * * * *